US00PP33419P3

(12) United States Plant Patent
Klemm et al.

(10) Patent No.: US PP33,419 P3
(45) Date of Patent: Aug. 31, 2021

(54) ***DIANTHUS* PLANT NAMED 'KLEDG20468'**

(50) Latin Name: ***Dianthus* L.**
Varietal Denomination: KLEDG20468

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/083,958

(22) Filed: Oct. 29, 2020

(65) Prior Publication Data

US 2021/0136977 P1 May 6, 2021

Related U.S. Application Data

(60) Provisional application No. 62/973,972, filed on Nov. 4, 2019.

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305
See application file for complete search history.

*Primary Examiner* — Anne Marie Grunberg
(74) *Attorney, Agent, or Firm* — Weatherly IP Solutions, LLC; Barbara Campbell

(57) ABSTRACT

A new *Dianthus* plant designated 'KLEDG20468' particularly distinguished by double purple-red flowers with pink borders and very early flowering, is disclosed.

1 Drawing Sheet

Genus and species: *Dianthus* L.
Variety denomination: 'KLEDG20468'.

BACKGROUND OF THE NEW PLANT

The present invention comprises a new and distinct variety of *Dianthus*, botanically known as *Dianthus* L., and hereinafter referred to by the variety name 'KLEDG20468'. 'KLEDG20468' originated from a naturally-occurring, whole plant mutation from the *Dianthus* parent 'KLEDG12163' (U.S. Plant Pat. No. 24,707) in May 2018 in The Netherlands.

In September 2018, 'KLEDG20468' was first vegetatively propagated by vegetative stem cuttings in Stuttgart, Germany, and subsequently in Latina, Italy. 'KLEDG20468' was found to reproduce true to type in successive generations of asexual propagation in Stuttgart, Germany and Latina, Italy via vegetative stem cuttings.

SUMMARY

The following are the most outstanding and distinguishing characteristics of 'KLEDG20468' when grown under normal horticultural practices in Stuttgart, Germany.

1. Double, purple-red flowers having a pink border; and
2. Very early flowering.

DESCRIPTION OF THE PHOTOGRAPH

This new *Dianthus* plant is illustrated by the accompanying photograph of plants grown in a greenhouse in Stuttgart, Germany. The colors shown are as true as can be reasonably obtained by conventional photographic procedures. The photograph is of a 30-week-old plant taken in May 2019 and is of a whole plant of 'KLEDG20468' showing the foliage, buds, and flowers.

DESCRIPTION

The following detailed descriptions set forth the distinctive characteristics of 'KLEDG20468'. The data which define these characteristics were collected from asexual reproductions carried out in Stuttgart, Germany. Data was collected in May 2019 on 7-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* L.
- *Common*.—Pot carnation.
- *Designation*.—'KLEDG20468'.

Parentage: Mutation parent is 'KLEDG12163' (U.S. Plant Pat. No. 24,707).

Plant:
- *Propagation type*.—Vegetative cuttings via stem, terminal cuttings.
- *Time to produce a rooted young plant*.—10 to 14 days.
- *Root description*.—Fine roots, young roots are RHS 161D, mature roots are RHS 199C.
- *Rooting habit shape*.—Lanceolate.
- *Plant form*.—Upright.
- *Plant height*.—15 cm to 17 cm.
- *Plant diameter or spread*.—22 cm to 25 cm.

Lateral branches/stems:
- *Shape of the branch in cross-section*.—Moderately angular.
- *Hollowness of the stem*.—Absent, solid.

*Length.*—7 cm to 10 cm.
*Diameter.*—4 cm to 7 cm.
*Internode length.*—2 cm to 3 cm.
*Internode quantity per branch.*—3 to 5.
*Number of internodes per branch/stem.*—3 to 5.
*Node length.*—0.2 cm to 0.4 cm.
*Node diameter.*—0.2 cm to 0.4 cm.
*Texture.*—Smooth.
*Color.*—RHS 146B.
*Flower clustering on the lateral branch.*—In some lateral branches.

Foliage:
*Arrangement.*—Opposite.
*Length.*—4 cm to 5 cm.
*Width.*—0.3 cm to 0.5 cm.
*Shape.*—Lanceolate.
*Apex.*—Acute.
*Base.*—Obtuse.
*Margin.*—Entire.
*Texture (both upper and lower surfaces).*—Smooth.
*Cross-section of the leaf.*—Moderately concave.
*Curvature of the leaf.*—Absent.
*Glaucosity of the leaf.*—Weak.
*Leaf color.*—Upper surface: Immature leaves are RHS 138A and mature leaves are RHS 137A. Lower surface: Immature leaves are RHS 138A and mature leaves are RHS 137A.
*Venation pattern.*—Absent.

Flowers:
*Flower type and habit.*—Semi-double, small sprays, round.
*Fragrance.*—Present.
*Position of the flowers compared to the foliage of the plant.*—Moderately above.
*Profile of both the upper and lower part in the lateral view.*—Convex.
*Diameter of the flower.*—1.8 cm to 2.2 cm.
*Natural flowering season.*—Spring to autumn.
*Position of flowers relative to the foliage.*—Moderately above.
*Number of flowers per spray.*—3 to 5.
*Flower longevity on the plant.*—14 to 18 days.

Buds:
*Length.*—0.5 cm to 1.5 cm.
*Diameter.*—0.3 cm to 0.4 cm.
*Shape.*—Elliptic.
*Color.*—RHS 138A.
*Extrusion of the styles at the bud stage.*—Absent.

Corolla:
*Quantity of petals and arrangement.*—7 to 13 and arranged in several whorls.
*Corolla height.*—0.8 cm to 1.5 cm.
*Petal length.*—1.8 cm to 2.5 cm.
*Petal width.*—1.0 cm to 1.5 cm.
*Petal shape.*—Spoon-shaped.
*Petal apex.*—Obtuse.
*Petal base.*—Acute.
*Petal margin.*—Serrated.
*Depth of petal margin.*—Shallow.
*Petal texture (both upper and lower surfaces).*—Smooth.
*Petal color (both immature and mature).*—Upper surface: RHS 58A with an RHS 68B border. Lower surface: RHS 69A.
*Macule.*—Present; around 0.7 cm in size and RHS 58A.
*Calyx.*—Quantity of sepals and arrangement: Composed of 5 sepals. Longitudinal axis of the lobes of the calyx: Straight. Shape: Campanulate. Calyx height: 0.8 cm to 1.5 cm. Calyx diameter (at the apex): 0.4 cm to 0.6 cm. Sepal texture (both upper and lower surfaces): Smooth. Sepal color: Upper surface: RHS 137A. Lower surface: RHS 137D.
*Position of the outer lobes of the epicalyx in relation to the calyx.*—Adpressed and free.
*Apex shape of the outer lobes of the epicalyx.*—Acute.
*Tip length of the outer lobes of the epicalyx.*—Short.
*Apex shape of the inner lobes of the epicalyx.*—Medium acuminate.
*Tip length of the inner lobes of the epicalyx.*—Short.

Peduncles:
*Length.*—5 cm to 8 cm.
*Diameter.*—0.2 cm.
*Strength.*—Moderate.
*Texture.*—Smooth.
*Color.*—RHS 146B.

Reproductive organs:
*Stamens.*—Quantity per flower: Moderate. Filament length: 0.5 cm to 0.8 cm. Filament color: RHS 157B. Anther length: 0.1 cm. Anther diameter: 0.05 cm. Anther color: RHS 155B. Pollen amount: Absent.
*Pistils.*—Not observed.

Fruit and seed set: Not observed.

Disease and pest/insect resistance: No disease and pest/insect resistance observed.

COMPARISON OF 'KLEDG20468' WITH PARENTAL LINE AND KNOWN VARIETY

'KLEDG20468' is distinguished from the mutation parent as described in Table 1.

TABLE 1

Comparison with Parental Line

| Characteristic | 'KLEDG20468' | Mutation Parent 'KLEDG12163' |
|---|---|---|
| Main flower color | RHS 58A | RHS 75B |
| Secondary flower color | RHS 68B | RHS 71A |
| Flower color pattern | Border | Bi-color |

'KLEDG20468' can be compared to the commercial *Dianthus* variety 'KLEDG18305' (U.S. Plant Pat. No. 31,019). Differences between the varieties are described in Table 2.

TABLE 2

Comparison with Similar Variety

| Characteristic | 'KLEDG20468' | 'KLEDG18305' |
|---|---|---|
| Flower type | Double | Single |
| Flower color | Purple-red with pink border | Pink with purple ring |
| Flowering time | Very early; around 195 days after potting (cold cultivation) | Early-medium; around 205 days after potting (cold cultivation) |

We claim:

1. A new and distinct variety of *Dianthus* plant designated 'KLEDG20468' as illustrated and described herein.

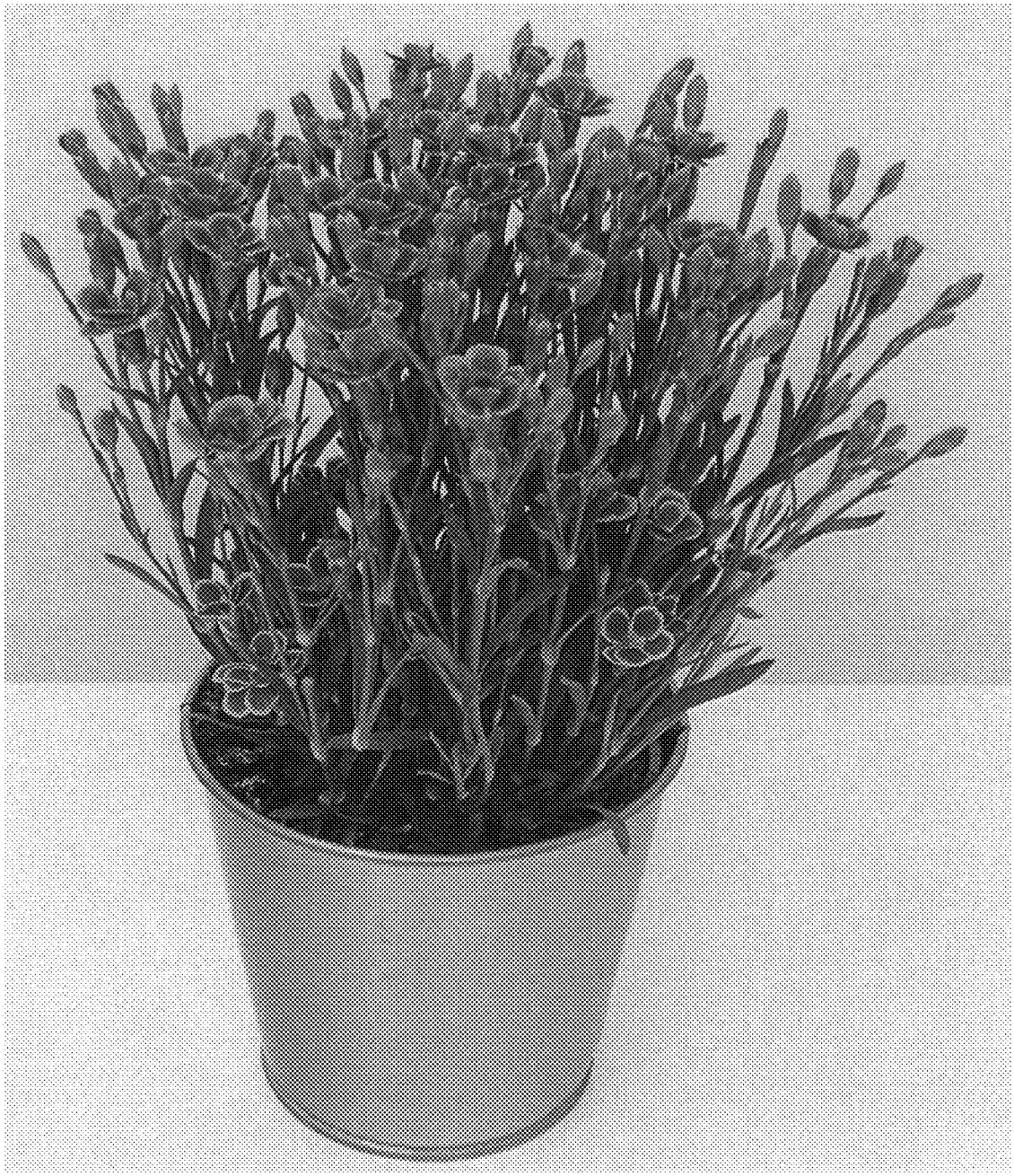

* * * * *